US010835344B2

(12) United States Patent
Barral et al.

(10) Patent No.: US 10,835,344 B2
(45) Date of Patent: Nov. 17, 2020

(54) DISPLAY OF PREOPERATIVE AND INTRAOPERATIVE IMAGES

(71) Applicant: Verily Life Sciences LLC, Mountain View, CA (US)

(72) Inventors: Joëlle K. Barral, Mountain View, CA (US); Martin Habbecke, Palo Alto, CA (US); Eric Johnson, Mountain View, CA (US); Francois Brahic, Mountain View, CA (US)

(73) Assignee: VERILY LIFE SCIENCES LLC, Mountain View, CA (US)

( * ) Notice: Subject to any disclaimer, the term of this patent is extended or adjusted under 35 U.S.C. 154(b) by 0 days.

(21) Appl. No.: 16/159,424

(22) Filed: Oct. 12, 2018

(65) Prior Publication Data
US 2019/0110855 A1 Apr. 18, 2019

Related U.S. Application Data

(60) Provisional application No. 62/573,321, filed on Oct. 17, 2017.

(51) Int. Cl.
*A61B 90/00* (2016.01)
*A61B 1/045* (2006.01)
(Continued)

(52) U.S. Cl.
CPC ............ *A61B 90/37* (2016.02); *A61B 1/0005* (2013.01); *A61B 1/00009* (2013.01); *A61B 1/04* (2013.01);
(Continued)

(58) Field of Classification Search
CPC ..... A61B 1/00009; A61B 1/0005; A61B 1/04; A61B 1/045; A61B 2090/365;
(Continued)

(56) References Cited

U.S. PATENT DOCUMENTS 7,831,294 B2 11/2010 Viswanathan
8,169,696 B2 5/2012 Yazdanfar et al.
(Continued)

FOREIGN PATENT DOCUMENTS

WO 2014/139021 A1 9/2014
WO 2015/121764 A1 8/2015
WO 2016/178690 A1 11/2016

OTHER PUBLICATIONS

International Search Report and Written Opinion from the International Searching Authority dated Jan. 7, 2019, for International Application No. PCT/US2018/055724, filed Oct. 12, 2018, 14 pages.
(Continued)

Primary Examiner — John R Schnurr
(74) Attorney, Agent, or Firm — Christensen O'Connor Johnson Kindness PLLC

(57) ABSTRACT

A system for video-assisted surgery includes one or more displays, a memory including at least one preoperative image, and a camera coupled to capture a video. A controller is coupled to the memory, the camera, and the one or more displays, and the controller includes logic that when executed by the controller causes the system to perform a variety of operations. The system may capture a video of a surgical area, including anatomical features, using the camera, and display the video of the surgical area on the one or more displays. The system may also display the at least one preoperative image on the one or more displays at the same time as the video. The location of the anatomical features shown in the video is displayed as an accentuated region on the at least one preoperative image.

21 Claims, 4 Drawing Sheets

(51) Int. Cl.
| | |
|---|---|
| G06T 19/00 | (2011.01) |
| G06T 7/00 | (2017.01) |
| G06T 7/70 | (2017.01) |
| G06T 19/20 | (2011.01) |
| A61B 34/30 | (2016.01) |
| H04N 7/18 | (2006.01) |
| A61B 1/00 | (2006.01) |
| A61B 1/04 | (2006.01) |
| A61B 34/20 | (2016.01) |
| H04N 5/225 | (2006.01) |

(52) U.S. Cl.
CPC .............. *A61B 1/045* (2013.01); *A61B 34/20* (2016.02); *A61B 34/30* (2016.02); *A61B 90/361* (2016.02); *G06T 7/0016* (2013.01); *G06T 7/70* (2017.01); *G06T 19/00* (2013.01); *G06T 19/20* (2013.01); *H04N 7/18* (2013.01); *A61B 2090/363* (2016.02); *A61B 2090/365* (2016.02); *A61B 2090/367* (2016.02); *A61B 2090/371* (2016.02); *A61B 2090/373* (2016.02); *A61B 2090/378* (2016.02); *A61B 2090/3762* (2016.02); *G06T 2207/10056* (2013.01); *G06T 2207/10068* (2013.01); *G06T 2207/10081* (2013.01); *G06T 2207/10088* (2013.01); *G06T 2207/10116* (2013.01); *G06T 2207/10132* (2013.01); *G06T 2207/20221* (2013.01); *G06T 2207/30004* (2013.01); *G06T 2219/004* (2013.01); *G06T 2219/2012* (2013.01); *H04N 2005/2255* (2013.01)

(58) Field of Classification Search
CPC ........ A61B 2090/367; A61B 2090/371; A61B 2090/373; A61B 2090/3762; A61B 2090/378; A61B 34/20; A61B 34/30; A61B 90/361; A61B 90/37; A61B 2090/363; G06T 19/00; G06T 19/20; G06T 2207/10056; G06T 2207/10068; G06T 2207/10081; G06T 2207/10088; G06T 2207/10116; G06T 2207/10132; G06T 2207/20221; G06T 2207/30004; G06T 2219/004; G06T 2219/2012; G06T 7/0016; G06T 7/70; G06T 7/0038; G06T 7/003; G06T 7/0033; G06T 7/0034; G06T 7/337; H04N 2005/2255; H04N 7/18
USPC ............................................ 348/65; 382/164
See application file for complete search history.

(56) References Cited

U.S. PATENT DOCUMENTS

| | | |
|---|---|---|
| 2006/0281971 A1 | 12/2006 | Sauer et al. |
| 2007/0060984 A1 | 3/2007 | Webb et al. |
| 2008/0033240 A1* | 2/2008 | Hoffman ................ A61B 34/70 600/109 |
| 2008/0243142 A1 | 10/2008 | Gildenberg |
| 2009/0292175 A1* | 11/2009 | Akimoto .............. A61B 1/2676 600/156 |
| 2011/0069159 A1 | 3/2011 | Soler et al. |
| 2011/0105895 A1 | 5/2011 | Kornblau et al. |
| 2011/0117025 A1 | 5/2011 | Dacosta et al. |
| 2013/0218024 A1 | 8/2013 | Boctor et al. |
| 2014/0022283 A1 | 1/2014 | Chan et al. |
| 2014/0133727 A1 | 5/2014 | Oktay et al. |
| 2014/0187967 A1 | 7/2014 | Wood et al. |
| 2014/0276008 A1 | 9/2014 | Steinbach et al. |
| 2015/0146946 A1 | 5/2015 | Elhawary et al. |
| 2015/0269741 A1* | 9/2015 | Moriya ................ G06T 7/0012 382/164 |
| 2016/0055268 A1* | 2/2016 | Bell ........................ G06F 30/13 703/1 |
| 2016/0100909 A1 | 4/2016 | Wollowick et al. |
| 2016/0353968 A1* | 12/2016 | Ikuma ................ A61B 1/00009 |
| 2017/0042631 A1 | 2/2017 | Doo et al. |
| 2017/0084036 A1* | 3/2017 | Pheiffer ................. G06T 7/337 |
| 2017/0172663 A1* | 6/2017 | Popovic .................... G06T 7/30 |
| 2017/0228877 A1* | 8/2017 | Ito ........................... A61B 34/10 |
| 2018/0189966 A1* | 7/2018 | Kamen .................. G06T 15/04 |

OTHER PUBLICATIONS

Wikipedia, the free encyclopedia, "Image-guided surgery", http://en.wikipedia.org/wiki/Image-guided_surgery, Last accessed Oct. 20, 2014, 2 pages.

Wikipedia, the free encyclopedia, "Fluorescence image-guided surgery", http://en.wikipedia.org/wiki/Fluorescence_image-guided_surgery, Last accessed Oct. 20, 2014, 4 pages.

Wikipedia, the free encyclopedia, "Endoscopy", http://en.wikipedia.org/wiki/Endoscopy, Last accessed Oct. 20, 2014, 7 pages.

Wikipedia, the free encyclopedia, "Laparoscopic surgery", http://en.wikipedia.org/wiki/Laparoscopic_surgery, Last accessed Oct. 20, 2014, 8 pages.

"UNC Laparoscopic Visualization Research", Augmented Reality Technology, University of North Carolina at Chapel Hill, Aug. 11, 1998, http://www.cs.unc.edu/Research/us/laparo.html, Last accessed Nov. 4, 2014, 4 pages.

* cited by examiner

DISPLAY OF PREOPERATIVE AND INTRAOPERATIVE IMAGES

REFERENCE TO RELATED APPLICATION

This application claims the benefit of U.S. Application No. 62/573,321, filed on Oct. 17, 2017, the contents of which are incorporated herein by reference.

TECHNICAL FIELD

This disclosure relates generally to systems for performing surgery, and in particular but not exclusively, it relates to robotic and endoscopic surgery.

BACKGROUND INFORMATION

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of open surgery, robotically controlled instruments may replace traditional tools to perform surgical motions. Feedback controlled motions may allow for smoother surgical steps than those performed by humans. For example, using a surgical robot for a step such as rib spreading, may result in less damage to the patient's tissue than if the step were performed by a surgeon's hand. Additionally, surgical robots can reduce the amount of time in the operating room by requiring fewer steps to complete a procedure.

However, robotic surgery may still be relatively expensive, and suffer from limitations associated with conventional surgery. For example, surgeons may become disoriented when performing robotic surgery, which may result in harm to the patient. Further, when parts of the body are deformed during surgery, the surgeon may not recognize them and unintentionally cut or damage tissue.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1A:
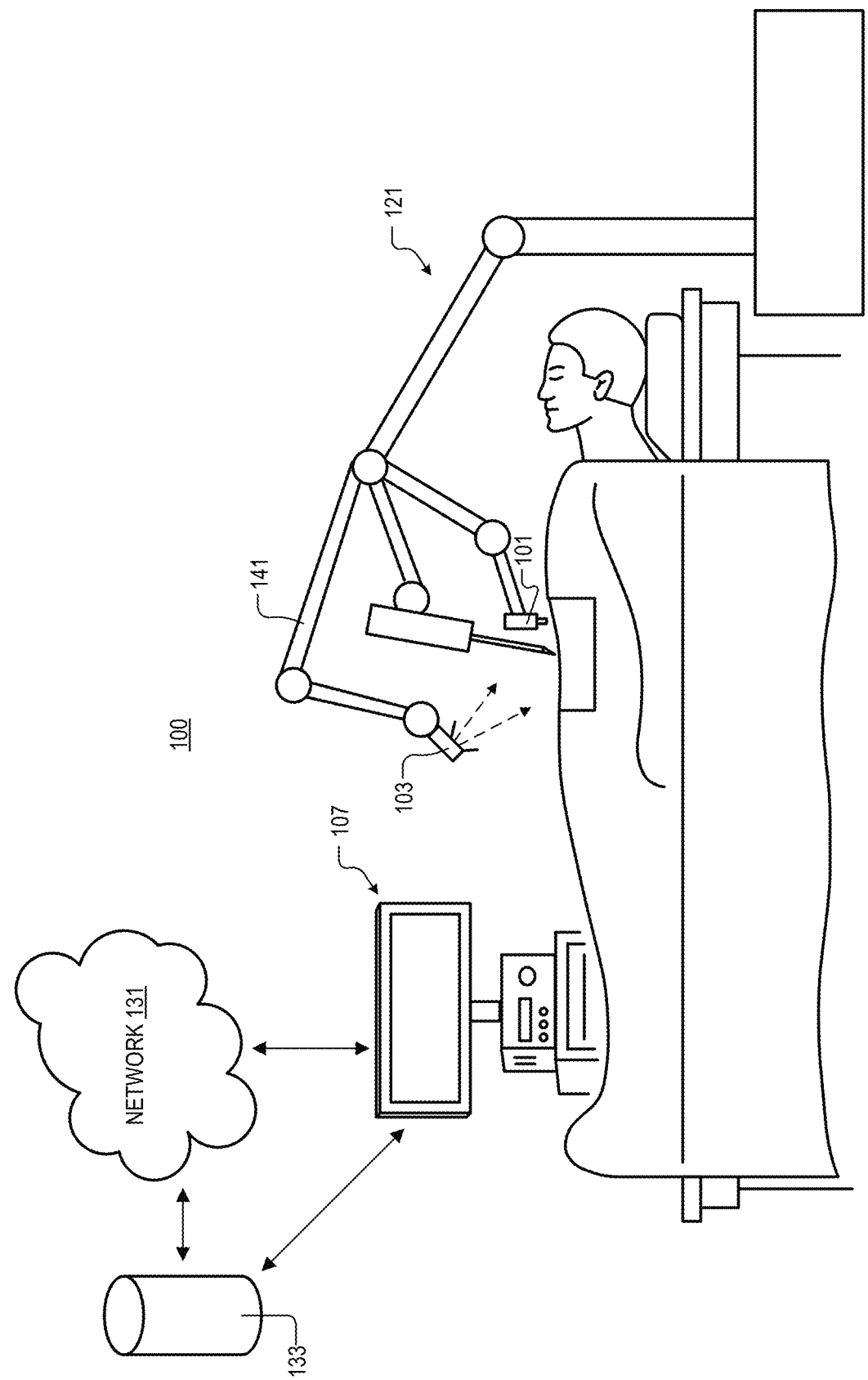
FIG. 1A illustrates a system for robotic video assisted surgery, in accordance with an embodiment of the disclosure.

Embodiments of an apparatus and method for the display of preoperative and intraoperative images are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

When a surgeon views preoperative images (e.g., X-rays, ultrasound, etc.) during a case, it is hard and time consuming for the surgeon to put them in the context of the intraoperative surgical field. This is partially because the surgeon is not used to reading radiological images, and partially because the structures are deformed intraoperatively (e.g., the abdomen is inflated, the table is inclined, dissection happens). Preoperative images, however, are hugely valuable to guide the procedure (e.g., by indicating the extent of tumor invasion, or providing anatomical clues as to what to expect behind currently dissected structures).

The instant disclosure provides a system and method for combining user input and automatic tracking of the procedure, as applied to the preoperative images. At a time $t=t_0$ (preoperative), the surgeon (or a member of the surgical staff) may open a 3D imaging dataset (e.g., a magnetic resonance image (MM), computerized tomography (CT) scan, ultrasound, X-ray, or the like) and adjust the slicing plane (e.g., zooming in or out; reformatting in axial, sagittal, coronal, or oblique orientations; etc.) such that the resulting 2D image best aligns with the current surgical field (which is captured by a camera). In case of deformation, various metrics for "best aligns" can be used (e.g., Dice coefficient). That metric can also be focused on a specific region of interest of the surgical field (e.g., the organ of interest).

The surgeon (or a member of the surgical staff, or potentially a remote radiologist) can then draw, on the preoperative image, the contour corresponding to the current video frame, or provide matching landmarks so anatomical features in the current video frame can be detected automatically and marked on the preoperative image. This may be accomplished using a custom made user interface or other input device (e.g., mouse, touch screen, keyboard, or the like).

At time $t>t_0$ (when surgery is being performed), that contour and the underlying preoperative image (properly zoomed in, reformatted, and oriented) may be automatically updated by combining information about the position of the camera and the stereo video feed in order to estimate the position difference between the new video frame and the reference one. Using the tracking of a surface element in the surgical video, the position of the features in the surgical video can be estimated along with the difference in location between the new video frame and the reference one. Additional information may also be used to calculate where the video is being imaged. The location of the features in the video may be accentuated on the preoperative image(s).

In one embodiment, the preoperative image or slicing plane for visualization may not be adjusted according to the current view of the surgical field. Instead a visualization of the endoscope and/or surgical tools may be displayed over the pre-op image (which is one example of accentuating anatomical features shown in the video). This allows the surgeon and/or the surgical staff to orient the pre-op image arbitrarily, but at the same time get a sense of the relation between pre-op image and surgical field. For instance, in a prostatectomy where the view of the endoscope camera is roughly aligned axially, the pre-op image can be viewed in a coronal orientation, enabling the system to display the locations of the endoscope and surgical tools in relation to the boundary of the prostate.

In some embodiments the reverse may occur: updating the surgical field based on the historical video stream while navigating within the preoperative images (e.g., if the radiologist is providing input that the surgeon wants to convert in his/her field of view). In such a case, the procedure is stopped while navigation happens.

The following disclosure will discuss the embodiments described above, as they relate to the embodiments shown in FIGS. 1A-3.

FIG. 1A illustrates system 100 for robotic video assisted surgery, in accordance with an embodiment of the disclosure. System 100 includes surgical robot 121 (including arms 141), camera 101 (e.g., CMOS image sensor or the like), light source 103 (e.g., one or more light emitting diodes, or the like), controller 107 (including a display), network 131 (e.g., one or more servers connected to the internet or local area network), and storage 133 (e.g., solid state memory or hard drives on servers). As shown, surgical robot 121 may be used to hold surgical instruments (e.g., each arm 141 holds an instrument at the distal ends of the arm) and perform surgery, diagnose disease, take biopsies, or conduct any other procedure a doctor could perform. Surgical instruments may include scalpels, forceps, cameras (e.g., camera 101) or the like. While surgical robot 121 only has three arms 141, one skilled in the art will appreciate that surgical robot 121 is merely a cartoon illustration, and that surgical robot 121 can take any number of shapes depending on the type of surgery needed to be performed and other requirements. Surgical robot 121 may be coupled to controller 107, network 131, and/or storage 133 either by wires or wirelessly. Furthermore, surgical robot 121 may be coupled (wirelessly or by wires) to a user input and controller to receive instructions from a surgeon or doctor. Controller 107, and the user of controller 107, may be located very close to the surgical robot 121 and patient (e.g., in the same room) or may be located many miles apart. Thus surgical robot 121 may be used to perform surgery where a specialist is many miles away from the patient, and instructions from the surgeon are sent over the internet or a secure network (e.g., network 131). Alternatively, the surgeon may be local and may simply prefer using surgical robot 121 because surgical robot 121 can better access a portion of the body than the hand of the surgeon could.

In the depicted embodiment storage 133 may be included in servers connected to the internet. Alternatively storage 133 maybe local storage such as a hard drive, solid state memory, or the like. Storage 133 may be coupled to network 131, which may include the internet or local area network. It is appreciated that storage 133 and network 131 may be considered part of controller 107. Thus controller 107 is a distributed system. Network 131 and storage 133 may provide logic to controller 107 that when executed by controller 107 causes system 100 to perform a variety of operations. Alternatively controller 107 may include the processor and memory of a general purpose computer.

In the depicted embodiment, a general purpose computer with a single display (including controller 107) is coupled to surgical robot 121. Controller 107 includes a memory including at least one preoperative image (e.g., X-ray image, a magnetic resonance image (MM), a computerized tomography (CT) image, or an ultrasound image). Camera 101 is coupled to capture a video of a surgical area, including anatomical features. The video of the surgical area is shown on the display(s) along with the at least one preoperative image. As will be shown in FIG. 1C, a location of the anatomical features shown in the video is displayed as an accentuated region on the at least one preoperative image. In some embodiments, displaying the at least one preoperative image includes changing a position of the accentuated region on the at least one preoperative image in real time, as the location of the anatomical features shown in the video changes over time. For example, if an open heart surgery is being performed and the camera is showing the left side of the heart, the preoperative image will show the left side of the heart accentuated; however, if camera 101 shifts to show the right side of the heart, the right side of the heart will be accentuated in the preoperative image.

Figure 1C:
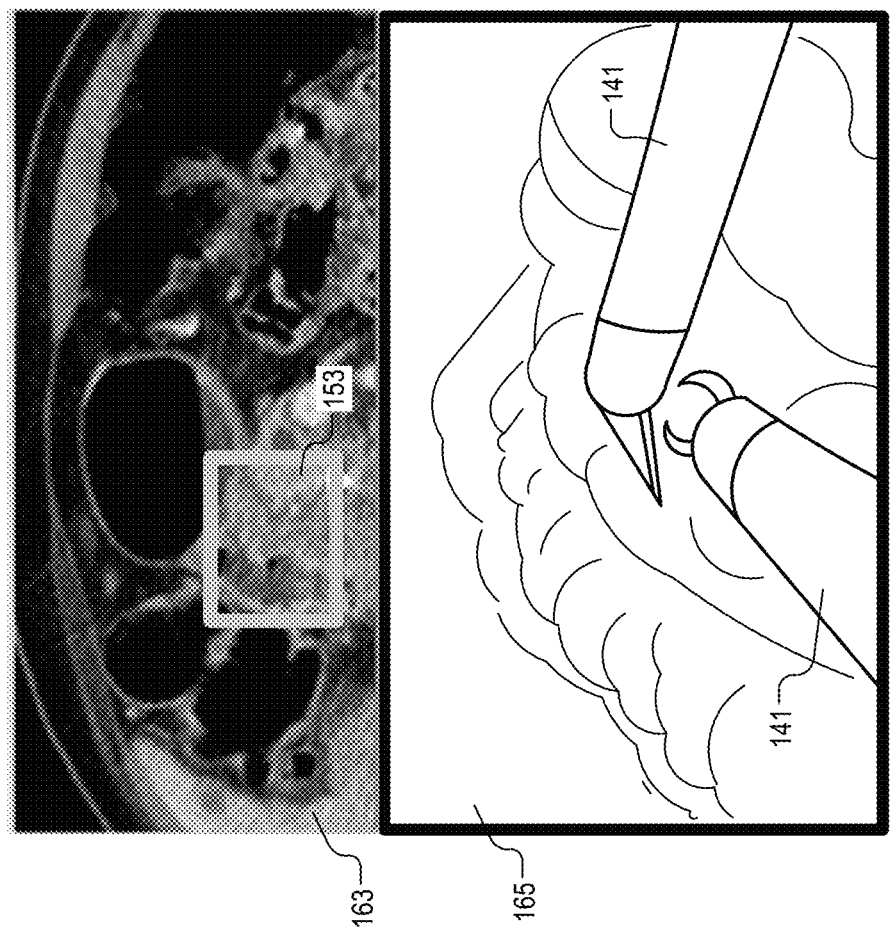
FIG. 1C illustrates at least one preoperative image displayed at the same time as a video of a surgical area, in accordance with an embodiment of the disclosure
Figure 1B:
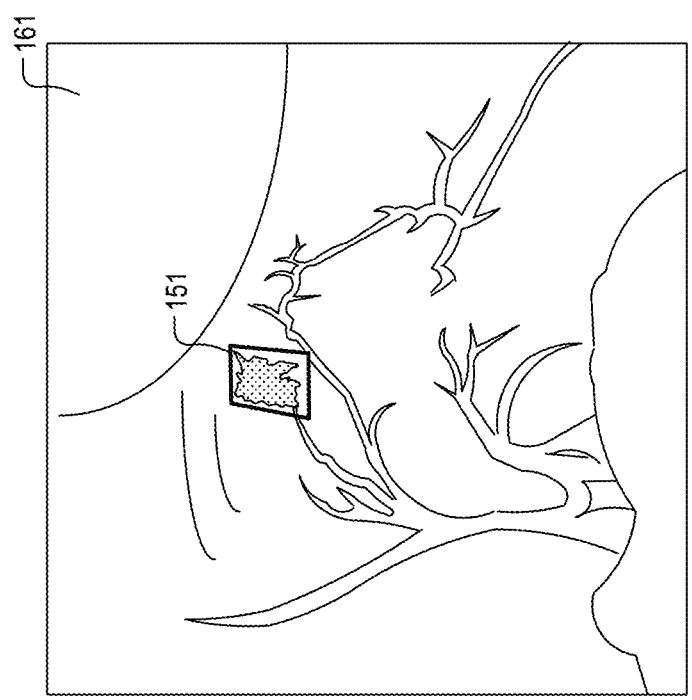
FIG. 1B illustrates tracking a surface element in a video, in accordance with an embodiment of the disclosure.

FIG. 1B illustrates tracking a surface element in a video, in accordance with an embodiment of the disclosure. FIG. 1B shows surface element 151 displayed on a surgical video captured by a camera (e.g., camera 101 in FIG. 1A). Surface element 151 may be used to track the position of the video in the body. For example, the camera can image surface element 151 and based on the location of surface element 151 in the video, the camera can determine where the video is imaging in the human body. The location of surface element 151 may be correlated with the location of features in the pre-op images. For example the location of the accentuated region in the at least one preoperative image may change based on the relative location of surface element 151 in the video. In one embodiment, surface element may be on a liver, and the video shifts to the right so that the surface element is on the far right side of the video feed. Accordingly, the annotated region on the preoperative image (s) may also shift to the right.

In some embodiments, surface element 151 may be identified by the user of the surgical robot (e.g., surgical robot 121), or the controller in the surgical robot may identify a number of surface elements autonomously to track the procedure. In the depicted embodiment, surface element 151 was chosen by a user and represents a unique piece of human anatomy.

It is appreciated that the surgical robot can track surface element 151 even when surface element 151 is moving. For example surface element 151 may be located on a lung and the lung is breathing. Similarly, surface element 151 may be located on the heart, and the heart is beating. Accordingly, surface element 151 will be moving throughout the image recognition processes, and the controller (coupled to the surgical robot and performing the image processing) can still determine the location of surface element 151 despite the movement.

In some embodiments, surface element 151 may be accentuated in the video. In the depicted embodiment, surface element 151 is highlighted using a bounding box surrounding surface element 151. Surface element 151 may be highlighted with comment box, bounding box, light contrast, dark contrast, or the like. However, in other embodiments, surface element 151 may not be highlighted in order to not distract surgeon while performing the surgery.

Accentuation of surface element 151 may be toggled on and off through voice control or other methods.

FIG. 1C illustrates at least one preoperative image 163 displayed at the same time as a video 165 (e.g., the video captured by camera 101 in FIG. 1A) of a surgical area, in accordance with an embodiment of the disclosure. As shown, the at least one preoperative image 163 is located above the video of the surgical area 165; however, in other embodiments preoperative image 163 may be located anywhere relative to the video of surgical area 165 including overlaid on video 165. In the depicted embodiment, the at least one preoperative image 163 is an MRI; however, in other embodiments the at least one preoperative image 163 may include an X-ray image, a CT image, or an ultrasound image. Within preoperative image 163 is accentuated region 153. Accentuated region 153 is identified using a bounding box. However, in other embodiments accentuated region 153 may include at least one of bordering the accentuated region with a line, changing a color of the accentuated region (e.g., with a semitransparent overlay or the like), changing a brightness of the accentuated region, or labeling the accentuated region.

In the depicted embodiment, the at least one preoperative image 163 includes a three dimensional preoperative model (here a 3D MRI). Although not amenable to illustration, orientation of the three dimensional preoperative model may change as the location of the anatomical features shown in the video changes with time. For example, if it becomes more desirable to show a different angle of preoperative image 163, preoperative image 163 may change the orientation of the MRI model.

In the video 165 of the surgical area, arms of the surgical robot 141 can be shown operating on tissue. The location of accentuated area 153 in preoperative image 163 automatically changes based on the location of the video 165. That way the surgeon knows where he or she is operating relative to other organs and structures in the body. The location of accentuated region 153 in the at least one preoperative image 163 may be determined by tracking a surface element (e.g., surface element 151 in FIG. 1B). The position and size of accentuated region 153 on preoperative image 163 may also be determined by the movement of arms 141 of the surgical robot (which may include motion tracking systems), as well as markers placed in the body, and/or by measuring distances using the camera. In some embodiments, the location of the surgical instruments in the body may be displayed on the preoperative image as the accentuated region.

Figure 2:
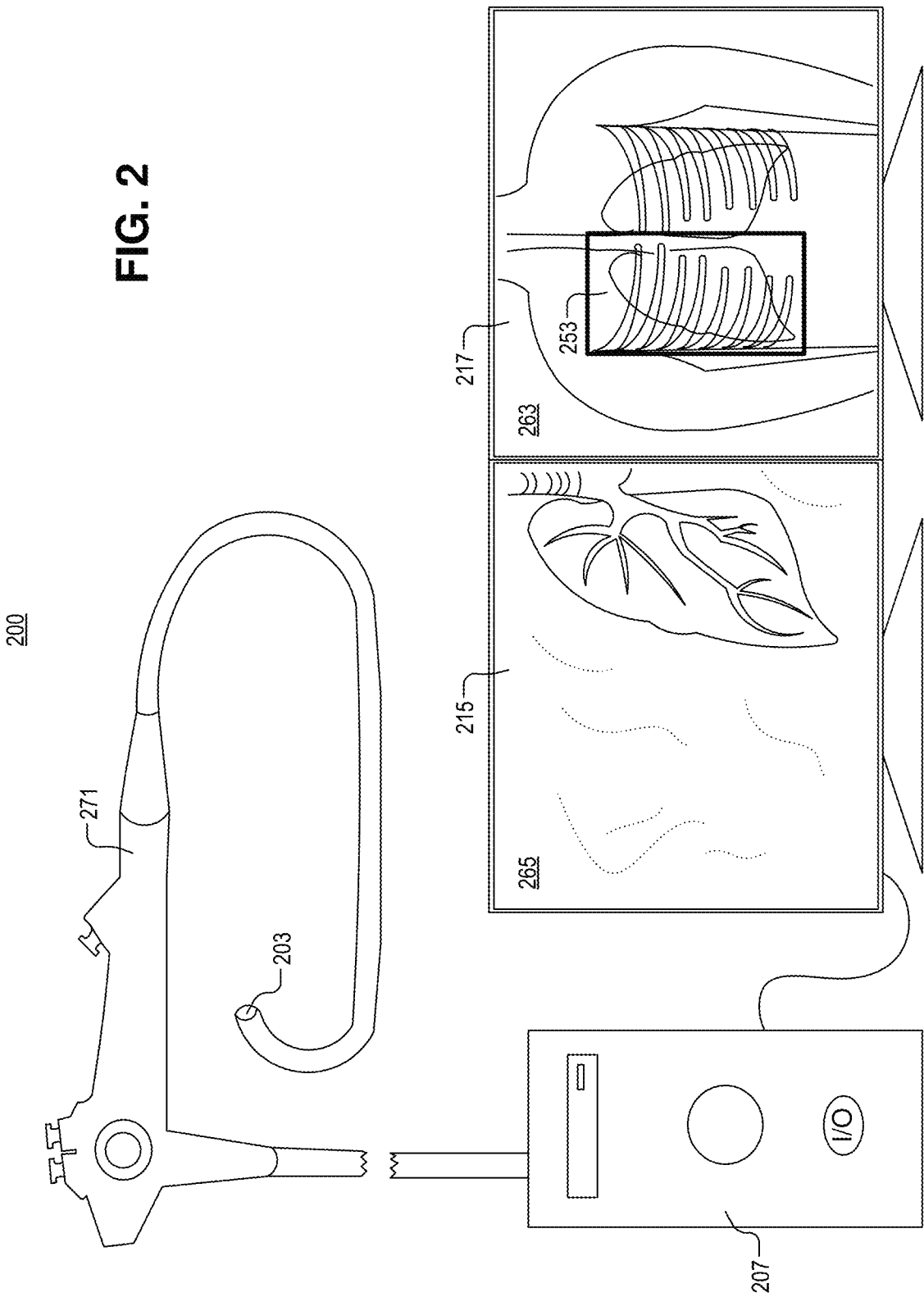
FIG. 2 illustrates a system for endoscopic video assisted surgery, in accordance with an embodiment of the disclosure.

FIG. 2 illustrates a system 200 for endoscopic video assisted surgery, in accordance with an embodiment of the disclosure. System 200 includes endoscope 271, controller 207, first display 215, and second display 217. Endoscope 271 is coupled to controller 207 (e.g., a general purpose computer) and includes camera 201 (e.g., a CMOS image sensor or the like) attached to the distal end of endoscope 271. The distal end of endoscope 271 is opposite the proximal end of endoscope 271, and may include one or more light sources such as light emitting diodes. The light emitted from endoscope 271 may be visible, infrared, ultraviolet, or the like. In the depicted embodiment, endoscope 271 is not shown inserted into a surgical area for simplicity of illustration. However, it is appreciated that the distal end of endoscope 271 may be inserted into a patient to provide the video 265 discussed in greater detail below.

First display 215 is coupled to the controller 207 to display a video 265 of a surgical area received from endoscope 271. In the depicted embodiment, the surgical area includes a lung. Second display 217 is coupled to controller 207 to display at least one preoperative image 263 stored in memory (e.g., RAM, ROM, etc.). In the depicted embodiment, preoperative image 263 includes a chest X-ray. The chest X-ray includes the same lung as shown in video 265. Preoperative image 263 includes an accentuated region 253 including a bounding box containing the lung shown in video 265. As the location of video feed 265 moves in the body of the patient, the accentuated region 265 will change location and size on preoperative image 263 (e.g., the bounding box may move, or grow larger or smaller depending on how "zoomed in" video 265 is). The size of the various videos and images displayed may be changed by the user (e.g., make the video/image windows larger or smaller).

Figure 3:
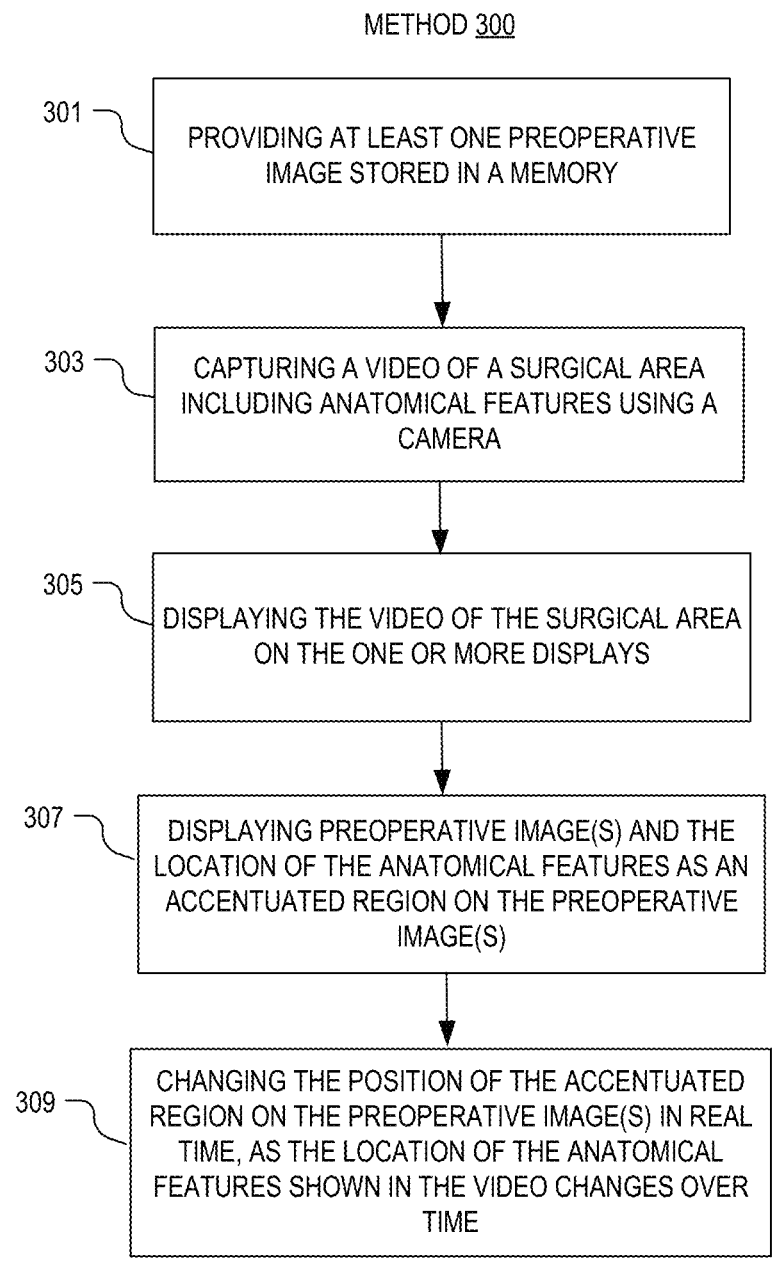
FIG. 3 illustrates a method of video assisted surgery, in accordance with an embodiment of the disclosure.

FIG. 3 illustrates a method of video-assisted surgery, in accordance with an embodiment of the disclosure. One of ordinary skill in the art having the benefit of the present disclosure will appreciate that blocks (301-309) in method 300 may occur in any order or even in parallel. Moreover, blocks may be added to, or removed from, method 300 in accordance with the teachings of the present disclosure.

Block 301 shows providing at least one preoperative image stored in a memory. The at least one preoperative image may include at least one of an X-ray image, a magnetic resonance image, a computerized tomography image, an ultrasound image, or the like. In microsurgery, the at least one image may include a microscopy image, or a pathology image. Further, the at least one preoperative image may include complex three dimensional models (e.g., a 3D reconstruction of a specific organ). One of ordinary skill in the art having the benefit of the present disclosure will appreciate there are many different types of preoperative imaging, and that many of them may be used in conjunction with the techniques described herein. It is further appreciated that a preoperative image includes any image captured before a surgical step is performed (e.g., including an image captured during a surgery).

In one embodiment, before the preoperative image is displayed to the surgeon, the surgeon (or the controller) may change the orientation of the at least one preoperative image to show the anatomical features in the preoperative image. Thus the surgeon sees the optimal view of the preoperative image while performing surgery.

Block 303 illustrates capturing a video of a surgical area including anatomical features using a camera, where the preoperative image includes at least part of the surgical area. In one embodiment, the camera may be included in an endoscope, and the endoscope may be used by a doctor to perform surgery. In other embodiments, the camera and the controller may be included in, or coupled to, a surgical robot.

Block 305 describes displaying the video of the surgical area on the one or more displays. In some embodiments, the video of the surgical area may share a screen with the preoperative images, while in other embodiments the video of the surgical area may be displayed on its own display. It is appreciated that a display includes a number of different devices such as flat panel displays, virtual reality headsets, tablets, and the like.

Block 307 shows displaying the at least one preoperative image on the one or more displays at the same time as the video. A location of the anatomical features (which may be identified using ICG or other contrast agents to visualize specific organs/anatomical structures and help with the localization of features) shown in the video is displayed as an accentuated region on the at least one preoperative image. In some embodiments, the location of the anatomical features, with respect to the preoperative image, may be tracked by identifying a surface element in the video, determining coordinates of the surface element in two successive frames in the video, and determining a change in the coordinates between the two successive frames. Thus, a feature in the video can be identified, and using changes in position of the feature in the video, the location of the accentuated region on the preoperative image can be changed accordingly. In some embodiments, a controller may be used to identify the surface element, or a user may select the surface element with a user interface.

In one embodiment the accentuated region may be accentuated using at least one of bordering the accentuated region with a line, changing a color of the accentuated region, changing a brightness of the accentuated region, or labeling the accentuated region.

In one embodiment, the preoperative image is superimposed on the video of the surgical area (e.g., via partial transparency, or image blending). This way the anatomical features in the preoperative image are "accentuated" by being overlaid on the video feed. However, the anatomical features may also be accentuated via other techniques described elsewhere.

Block 309 illustrates changing a position of the accentuated region on the preoperative image(s) in real time, as the location of the anatomical features shown in the video changes over time. In one embodiment, the preoperative image(s) includes a three dimensional preoperative model, and displaying the preoperative image(s) on the one or more displays at the same time as the video includes changing an orientation of the three dimensional preoperative model as the location of the anatomical features shown in the video changes over time. For example, the at least one preoperative image may include a 3D MRI scan. As the location of the place in the body where the video is being captured changes (e.g., because the camera moved to show new organs, etc.) the orientation of the 3D MRI model may change to show the new video location. Thus, the surgeon is provided the accentuated region highlighting the organs shown in the video, and also the preoperative model is orienting itself to better show images of the organs in the preoperative image(s). Changes to the preoperative image(s) may be achieved by the system recognizing different organs/anatomical features or fiducial markers (e.g., surgical clips or the like), using computer vision systems. Recognition of organs/fiducial markers may be performed at least in part by machine learning algorithms (e.g., a convolutional neural network trained to recognize specific features, recurrent neural network, long short-term memory network, or the like), and object tracking may be used to shift views.

In one embodiment, the user may select an order of images the surgeon wishes to see, and "tie" these images to various steps in the surgery. For instance, in a surgery involving multiple organs (e.g., lung and lymph nodes), the surgeon may want to see preoperative images of the lung while operating on the lung, and a different preoperative image of lymph nodes while operating on lymph nodes. In this embodiment, the system may recognize (e.g., using the machine vision techniques or fiducial markers described herein) when the surgeon has switched from operating on the lung to operating on the lymph nodes, and the system will display the preoperative image(s) of the lymph nodes. Prior to the surgery, the surgeon or surgical team may "tie" certain images to certain events in the surgery, therefore the preoperative images will be displayed in response to certain events occurring (e.g., when an organ comes into view of the video feed, after a certain amount of time has elapsed, when a specific instrument is being used (e.g., a stapler), when a marker is placed, when the user of the system instructs the system to switch preoperative images, etc.).

In some embodiments, the surgeon may "tie" the preoperative image to fiducial markers placed in the body. For instance, when a fiducial marker comes into view the system may change the preoperative image displayed (e.g., switch to a different image, update its orientation, magnification level, or the like). In some embodiments, the camera capturing the surgical video may move to always show the tips of the instruments or other important aspect of the surgery (e.g., the organ being operated on), and the preoperative image may also move to include the important location and be displayed in the right orientation. This may be achieved by correlating the amount of motion of the camera and/or surgical instruments to a corresponding change to the preoperative image to show the same relative location. In one embodiment, the preoperative image could also be scaled/stretched to map the anatomy (e.g., lungs being operated on might be collapsed, accordingly, the preoperative image is similarly altered to reflect the collapsed state).

In one embodiment, when the application to show the video of the surgical area and the preoperative image is initiated, the system may recognize the preferred sizing, location, or frame of the preoperative image that the surgeon likes to first look at. The system may then display this specific image to the user of the system. For example, when performing a specific type of lobectomy, there may be a CT scan of the lung. The surgeon may always like to begin a surgery by examining a sagittal view and slice near the middle of the 3D CT scan. Accordingly the system may recognize the surgeon's preferences and display the appropriate image. Recognition of preferences may be performed using a machine learning algorithm that is trained with user log in information (e.g., the specific user using the system), the preoperative images selected, the time when the preoperative images are selected (e.g., relative time to other events or absolute time), the type of surgery to be performed (which may be input into the system prior to the surgery or identified using a machine learning algorithm), or the like. The system may perform other analysis about how the surgeon is using the application and apply settings accordingly.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise. Processes may also occur locally or across distributed systems (e.g., multiple servers).

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for video-assisted surgery, comprising:
   one or more displays;
   a memory including at least one preoperative image stored thereon;
   a camera configured to capture a video; and
   a controller coupled to the memory, the camera, and the one or more displays, wherein the controller includes logic that when executed by the controller causes the system to perform operations including:
   capturing the video of a surgical area, including anatomical features, using the camera;
   displaying the video of the surgical area on the one or more displays; and
   displaying the at least one preoperative image on the one or more displays at the same time as the video, wherein a location of the anatomical features shown in the video is displayed as an accentuated region on the at least one preoperative image, wherein displaying the at least one preoperative image includes changing a position of the accentuated region on the at least one preoperative image in real time, as the location of the anatomical features shown in the video changes over time;
   identifying a surface element in the video;
   determining coordinates of the surface element in two successive frames in the video; and
   determining a difference in the coordinates between the two successive frames.

2. The system of claim 1, wherein the at least one preoperative image includes a three dimensional preoperative model, and wherein displaying the at least one preoperative image includes changing an orientation of the three dimensional preoperative model as the location of the anatomical features shown in the video changes over time.

3. The system of claim 1, wherein the controller further includes logic that when executed by the controller causes the system to perform operations including:
   changing a position of the accentuated region on the at least one preoperative image in response to determining the change in the coordinates.

4. The system of claim 1, wherein the controller further includes logic that when executed by the controller causes the system to perform operations including accentuating the surface element in the video.

5. The system of claim 1, wherein the camera is included in an endoscope, and wherein the endoscope is coupled to the controller.

6. The system of claim 1, wherein the camera and the controller are coupled to a surgical robot, wherein the controller further includes logic that when executed by the controller causes the system to perform operations including controlling the movement of one or more arms of the surgical robot.

7. The system of claim 1, wherein the accentuated region includes at least one of bordering the accentuated region with a line, changing a color of the accentuated region, changing a brightness of the accentuated region, or labeling the accentuated region.

8. The system of claim 1, wherein the at least one preoperative image includes at least one of an X-ray image, a magnetic resonance image, a computerized tomography image, microscopy image, pathology image, or an ultrasound image.

9. The system of claim 1, wherein the at least one preoperative image includes a three-dimensional preoperative model, and wherein displaying the at least one preoperative image on the one or more displays at the same time as the video includes changing an orientation of the three-dimensional preoperative model independently of an orientation of the video of the surgical area.

10. The system of claim 1, wherein the controller further includes logic that when executed by the controller causes the system to perform operations including:
    changing a location of the accentuated region based on a relative location of the surface element in the video.

11. A method of video-assisted surgery, comprising:
    providing at least one preoperative image stored in a memory;
    capturing a video of a surgical area including anatomical features using a camera, wherein the preoperative image includes at least part of the surgical area;
    displaying the video of the surgical area on the one or more displays; and
    displaying the at least one preoperative image on the one or more displays at the same time as the video, wherein a location of the anatomical features shown in the video is displayed as an accentuated region on the at least one preoperative image, wherein displaying the at least one preoperative image includes changing a position of the accentuated region on the at least one preoperative image in real time, as the location of the anatomical features shown in the video changes over time;
    identifying a surface element in the video;
    determining coordinates of the surface element in two successive frames in the video; and
    determining a difference in the coordinates between the two successive frames.

12. The method of claim 11, wherein identifying the surface element includes using at least one of a controller to identify the surface element, or having a user select the surface element with a user interface.

13. The method of claim 11, further comprising:
    changing a position of the accentuated region on the at least one preoperative image in response to determining the change in the coordinates.

14. The method of claim 11, wherein the at least one preoperative image includes a three dimensional preoperative model, and wherein displaying the at least one preoperative image on the one or more displays at the same time as the video includes changing an orientation of the three dimensional preoperative model as the location of the anatomical features shown in the video changes over time.

15. The method of claim 11, wherein capturing a video of a surgical area includes capturing the video with an endoscope, and wherein the camera is disposed in the endoscope.

16. The method of claim 11, wherein capturing a video of a surgical area includes capturing the video with a surgical robot, wherein the camera is coupled to the surgical robot.

17. The method of claim 11, wherein the accentuated region includes at least one of bordering the accentuated region with a line, changing a color of the accentuated region, changing a brightness of the accentuated region, or labeling the accentuated region.

18. The method of claim 11, wherein the at least one preoperative image includes at least one of an X-ray image, a magnetic resonance image, a computerized tomography image, or an ultrasound image.

19. The method of claim 11, further comprising changing the orientation of the at least one preoperative image to show the anatomical features in the preoperative image, prior to displaying the at least one preoperative image on the one or more displays at the same time as the video.

20. The method of claim 11, wherein the preoperative image is superimposed on the video.

21. A system for video-assisted surgery, comprising:
- one or more displays;
- a memory including at least one preoperative image stored thereon;
- a camera configured to capture a video; and
- a controller coupled to the memory, the camera, and the one or more displays, wherein the controller includes logic that when executed by the controller causes the system to perform operations including:
  - capturing the video of a surgical area, including anatomical features, using the camera;
  - displaying the video of the surgical area on the one or more displays; and
  - displaying the at least one preoperative image on the one or more displays at the same time as the video, wherein a location of the anatomical features shown in the video is displayed as an accentuated region on the at least one preoperative image, wherein displaying the at least one preoperative image includes changing a position of the accentuated region on the at least one preoperative image in real time, as the location of the anatomical features shown in the video changes over time, wherein displaying the at least one preoperative image includes changing a position of the accentuated region on the at least one preoperative image in real time, as the location of the anatomical features shown in the video changes over time;
- identifying a surface element in the video;
- determining coordinates of the surface element in two successive frames in the video; and
- determining a difference in the coordinates between the two successive frames.

* * * * *